US007426345B2

(12) United States Patent  
Takamatsu et al.

(10) Patent No.: US 7,426,345 B2
(45) Date of Patent: Sep. 16, 2008

(54) SLIDE PHOTOGRAPH DATA CREATION SYSTEM, AND SLIDE PHOTOGRAPH DATA

(75) Inventors: Terumasa Takamatsu, Hirosaki (JP); Tatsusuke Sato, Hirosaki (JP); Tomisato Miura, Hirosaki (JP); Hiroyuki Nozaka, Hirosaki (JP); Hidekatsu Yasuike, Zama (JP); Hiromi Miura, Aomori-ken (JP); Zheng Zhongxi, Fremont, CA (US)

(73) Assignee: Claro Inc., Hirosaki-Shi, Aomori-Ken (JP)

( * ) Notice: Subject to any disclaimer, the term of this patent is extended or adjusted under 35 U.S.C. 154(b) by 289 days.

(21) Appl. No.: 11/241,942

(22) Filed: Oct. 4, 2005

(65) Prior Publication Data  
US 2006/0228107 A1    Oct. 12, 2006

(30) Foreign Application Priority Data  
Apr. 11, 2005  (JP) ............................ 2005-113354

(51) Int. Cl.  
*H04N 7/18* (2006.01)  
*H04N 9/47* (2006.01)  
*G02B 21/36* (2006.01)  
*G02B 23/00* (2006.01)  
*G02B 21/26* (2006.01)  
*G06K 9/00* (2006.01)  
*G09G 5/00* (2006.01)  
*B65G 1/00* (2006.01)

(52) U.S. Cl. .................. 396/432; 348/79; 359/392; 359/393; 382/154; 345/629; 414/331.14

(58) Field of Classification Search .............. 348/42, 348/44, 51, 53, 79, 231.2, 231.3, 333.05; 396/432; 359/363, 368–398; 211/41.1, 41.8, 211/41.14; 414/331.14; 345/629; 356/609; 382/154  
See application file for complete search history.

(56) References Cited  
U.S. PATENT DOCUMENTS

| 4,554,638 | A | * | 11/1985 | Iida | 345/658 |
| 4,661,986 | A | * | 4/1987 | Adelson | 382/154 |
| 4,818,169 | A | * | 4/1989 | Schram et al. | 414/331.18 |
| 5,963,368 | A | * | 10/1999 | Domanik et al. | 359/396 |
| 6,331,860 | B1 | * | 12/2001 | Knox | 345/620 |
| 6,507,358 | B1 | * | 1/2003 | Mori et al. | 348/42 |

(Continued)

FOREIGN PATENT DOCUMENTS

EP    1 324 097 A1    12/2002

*Primary Examiner*—W. B. Perkey  
*Assistant Examiner*—Andrew Williams  
(74) *Attorney, Agent, or Firm*—Manabu Kanesaka

(57) ABSTRACT

A slide photograph data creation system includes a digital camera for making high-magnification photographs of samples, a sample transporter for holding and transporting samples, a controller for controlling the camera and the sample transporter so as to provide overlapping photographs, a pasting information generator for recognizing the margin by which the photographs overlap and for generating pasting-together information, and a photograph file generator for storing in a single file a plurality of high-magnification photographs and the pasting-together information. The system facilitates the examination and photography of large numbers of samples, and enables discrimination of the three-dimensional structure of a sample. Since the photographic data is managed with a database, virtual slide photographs and their attributes information can be browsed over a network or the Internet.

11 Claims, 15 Drawing Sheets

U.S. PATENT DOCUMENTS

| | | | |
|---|---|---|---|
| 6,588,605 B1 * | 7/2003 | Volkert et al. | 211/41.14 |
| 6,683,649 B1 * | 1/2004 | Anderson | 348/333.05 |
| 6,693,716 B2 * | 2/2004 | Sieckmann | 356/609 |
| 6,847,481 B1 * | 1/2005 | Ludl et al. | 359/391 |
| 2002/0039434 A1 | 4/2002 | Levin et al. | |
| 2003/0184855 A1 * | 10/2003 | Yasuda et al. | 359/383 |
| 2004/0114218 A1 | 6/2004 | Karlsson et al. | |
| 2004/0119817 A1 * | 6/2004 | Maddison et al. | 348/79 |
| 2004/0189674 A1 * | 9/2004 | Zhang et al. | 345/629 |

* cited by examiner

SLIDE PHOTOGRAPH DATA CREATION SYSTEM, AND SLIDE PHOTOGRAPH DATA

BACKGROUND OF THE INVENTION AND RELATED ART STATEMENT

The present invention relates to a slide picture, i.e., photograph, data creation system and slide picture data. In particular, the present invention relates to a slide picture data creation system for setting preparates (slide glass) containing samples in microscopes, photographing the samples at high magnification, and generating and managing slide picture data, in pathological histological studies, hematological studies, genetic studies, cytological studies, and the like, as well as the generated slide picture data.

Recently, pathological histological, hematological, and genetic microscopic studies, and the like, have been performed by photographing samples of extracted pathological tissues and cells and blood, and the like, with a photographic apparatus equipped on a microscope, taking the pictures into a computer, and creating picture data that can be observed on a display. Such technology is described in, for example, Japanese Unexamined Patent Publication No. 2003-222801.

In the above-mentioned conventional system, the work of setting preparates containing samples of pathological tissues, and the like, in the microscope and then replacing the preparates with others was performed manually. When creating large numbers of picture data, much time and labor was expended for replacement of the preparates. Also, in order to open and process large numbers of picture files when creating and browsing the pictures, a large amount of memory was necessary, and substantial processing time was required. Also, because basically only two-dimensional picture information could be photographed, the sample structure on the Z axis parallel to the optical axis of the microscope could not be discriminated from the photographed picture.

An object of the present invention, therefore, is to eliminate the aforementioned problems associated with the prior art, and to provide a slide picture data creation system that can automatically and efficiently perform the operation of supplying to a microscope large numbers of preparates containing samples such as pathological tissues.

An object of the present invention is also to generate rapidly and automatically the slide picture data, including a plurality of photographs of the necessary parts of the samples at high magnification by the microscope, as well as to provide the generated slide picture data.

Further objects and advantages of the invention will be apparent from the following description of the invention and the associated drawings.

SUMMARY OF THE INVENTION

The slide picture data creation system according to the present invention includes a digital photography means, which is provided in a microscope and photographs high-magnification pictures; a sample transport means, which holds samples and is capable of moving three-dimensionally; a photography control means, which controls the digital photography means to photograph a plurality of high-magnification pictures while controlling the sample transport means to successively move samples perpendicularly to the optical axis of the microscope so that a margin for pasting, which is a location where a picture overlaps with another picture is present; a pasting-together information generation means, which recognizes the margin for pasting by picture processing from the plurality of high-magnification pictures, and generates pasting-together information of plural high-magnification pictures; and a picture file generation means, which stores in a single file the plural high-magnification pictures and the pasting-together information.

Another aspect of the slide picture data creation system is that plural pictures are photographed at a prescribed interval while also moving minutely in a direction parallel to the optical axis of the microscope. The system also includes a focal position detection means, which detects a position where the focus of the microscope is matched in a direction parallel to the optical axis of the microscope.

The slide picture data creation system further includes a thumbnail picture generation means, which generates thumbnail pictures, i.e., reduced-size pictures of an entire picture, made by pasting together high-magnification pictures. The system also includes an external digital camera means. Another aspect of the system is that pictures photographed by the external digital camera, the plural high-magnification pictures, and the pasting-together information are stored by being combined in a single motion picture file.

The slide picture data creation system further includes a photographic area automatic recognition means, which automatically determines an area in which to photograph a high-magnification picture from a picture made by the external digital camera. The system further includes a photographic area semi-automatic recognition means, which list-displays pictures photographed by the external digital camera of plural preparates, together with a photographic area recognized by the photographic area automatic recognition means, and therefore enables the user to correct the photographic area.

The system further includes a picture publishing means, which registers files of photographed pictures in a database, and enables the searching and referencing of pictures over a network.

The sample transport means includes a first guide member, which is provided in a fixed position on a stand; a first movable body, which is supported to be guided on the first guide member and is capable of horizontal movement in the front-back direction of the stand; a second guide member, which is provided on the first movable body; a second movable body, which is supported to be guided on the second guide member and is capable of horizontal movement in the left-right direction of the stand; and a preparate holding hand, which is capable of ascending and descending movement on the second movable body, and which has a pair of finger parts which respectively support two ends of a preparate horizontally from beneath. The preparate holding hand has on the upper side of at least one of the finger parts a suction hole communicating with a negative pressure source for suction-holding the preparate.

The sample transport means furthermore includes a third guide member, which is provided in a fixed position on the stand; a third movable body, which is supported to be guided on the third guide member and is capable of ascending and descending movement on the stand; and a preparate storage magazine, which is supported on the third movable body and has a pair of side wall plates having plural preparate holding slots arranged in parallel vertically for holding two ends of a preparate that can be inserted and removed. The magazine is configured so as to be capable of receiving plural preparates arranged vertically in a shelf-like manner at an interval such that the finger parts of the preparate holding hand can be inserted and removed.

Another aspect of the present invention is that the preparate storage magazine is capable of being freely attached to and detached from the third movable body. The preparate storage magazine includes an attachment/detachment lever, which is capable of being manually switched for displacement between a locked position, where it is fixed to the third movable body, and an unlocked position, where it becomes separable from the third movable body; and a movable stopper, which is operationally linked to the movement of the attachment/detachment lever so as to be in a position preventing slipping-out of the preparates from the preparate storage magazine when the attachment/detachment lever is in the unlocked position, and to be in a position enabling insertion and removal of preparates when the attachment/detachment lever is in the locked position.

Still another aspect of the present invention is that plural high-magnification pictures and pasting-together information of the pictures can be collected and stored in a single motion picture file.

As a result of the present invention, it is possible to photograph at high speed only the areas necessary for photography by microscope. Furthermore, by storing the picture data in one file, there is no need to open and process large numbers of picture files when browsing, a large amount of memory is not necessary, and high-speed processing and display are possible.

Also, as a result of the present invention, by scanning the focal position and photographing in the direction of the Z axis, the three-dimensional structure of a sample can be discriminated. For example, discrimination as to whether the shape of a cell nucleus is a true sphere or an elliptical sphere, which is often necessary for diagnosis, becomes possible. Furthermore, the picture data is managed with a database, and virtual slide pictures and their attributes information can then be browsed over a network or the web.

Also, the work of removing sample preparates stored in the preparate storage magazine, moving them between the object lens and the condenser lens of the microscope, and again returning the preparates to the storage magazine upon having finished examination and photography, can be performed automatically. It becomes possible, therefore, to efficiently perform the work of examination and photography of large numbers of samples.

Also, because the preparate storage magazine can be separated, the operations of insertion and removal of sample preparates into and from the preparate storage magazine become easier. In addition, by preparing plural preparate storage magazines and using these by successive replacement, it becomes possible to perform examination and photography of large numbers of samples more efficiently.

Furthermore, when separating and carrying the preparate storage magazine, any accidents such as having the front face of the magazine be accidentally turned downward, and having the precious samples fall from the magazine, can be avoided.

DETAILED DESCRIPTION OF PREFERRED EMBODIMENTS

In the following description, embodiments of the present invention will be explained with reference to the associated drawings.

The slide picture data creation system of the present invention includes a preparate photography system and a computer for control and picture processing. In the following description, first the structure and mechanisms of the preparate photography system of the present invention are explained, and then the processing functions of the computer for control and picture processing are explained.

Figure 1:
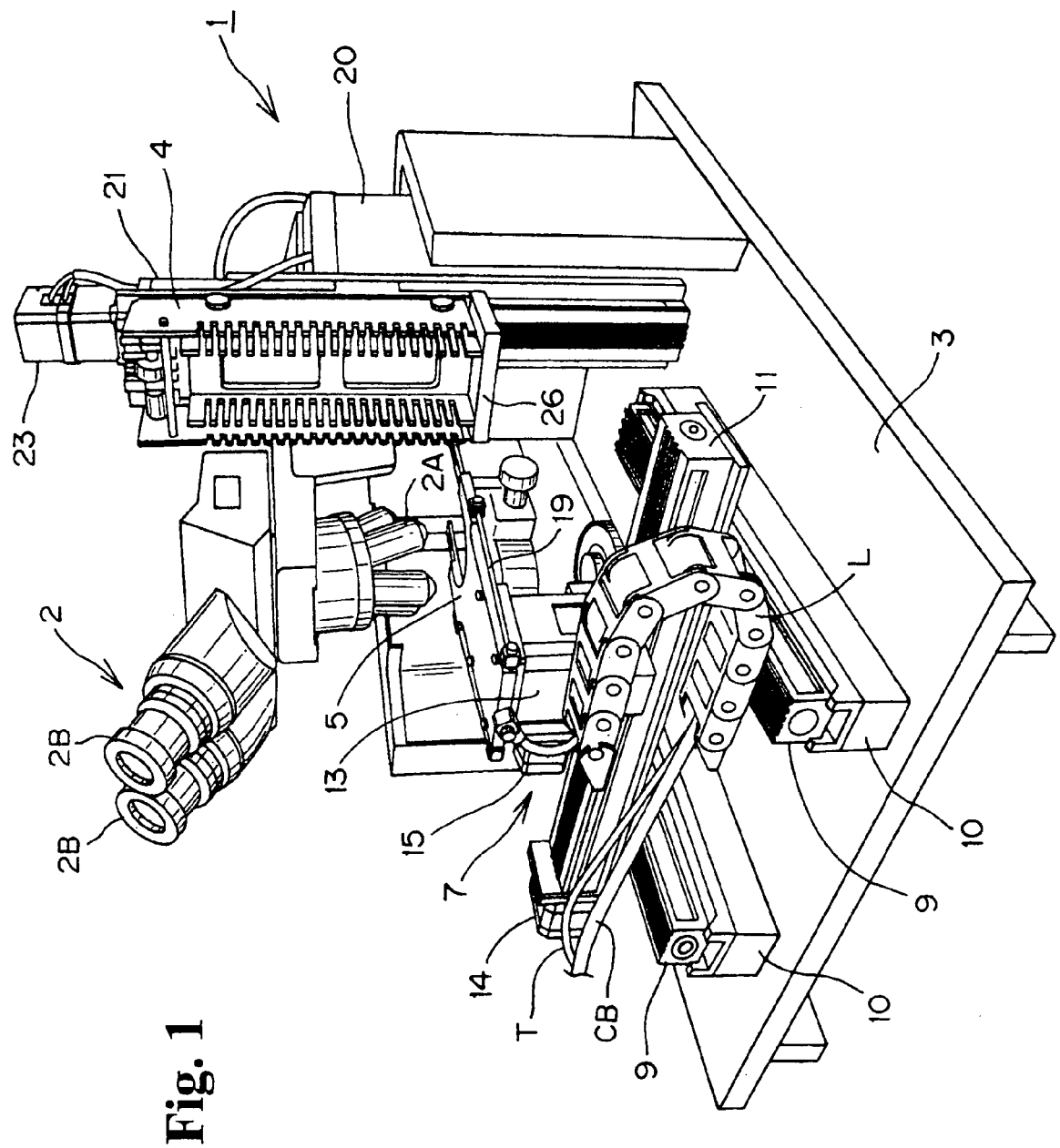
FIG. 1 is a perspective view showing the structure of a preparate photography system of the present invention.
Figure 2:
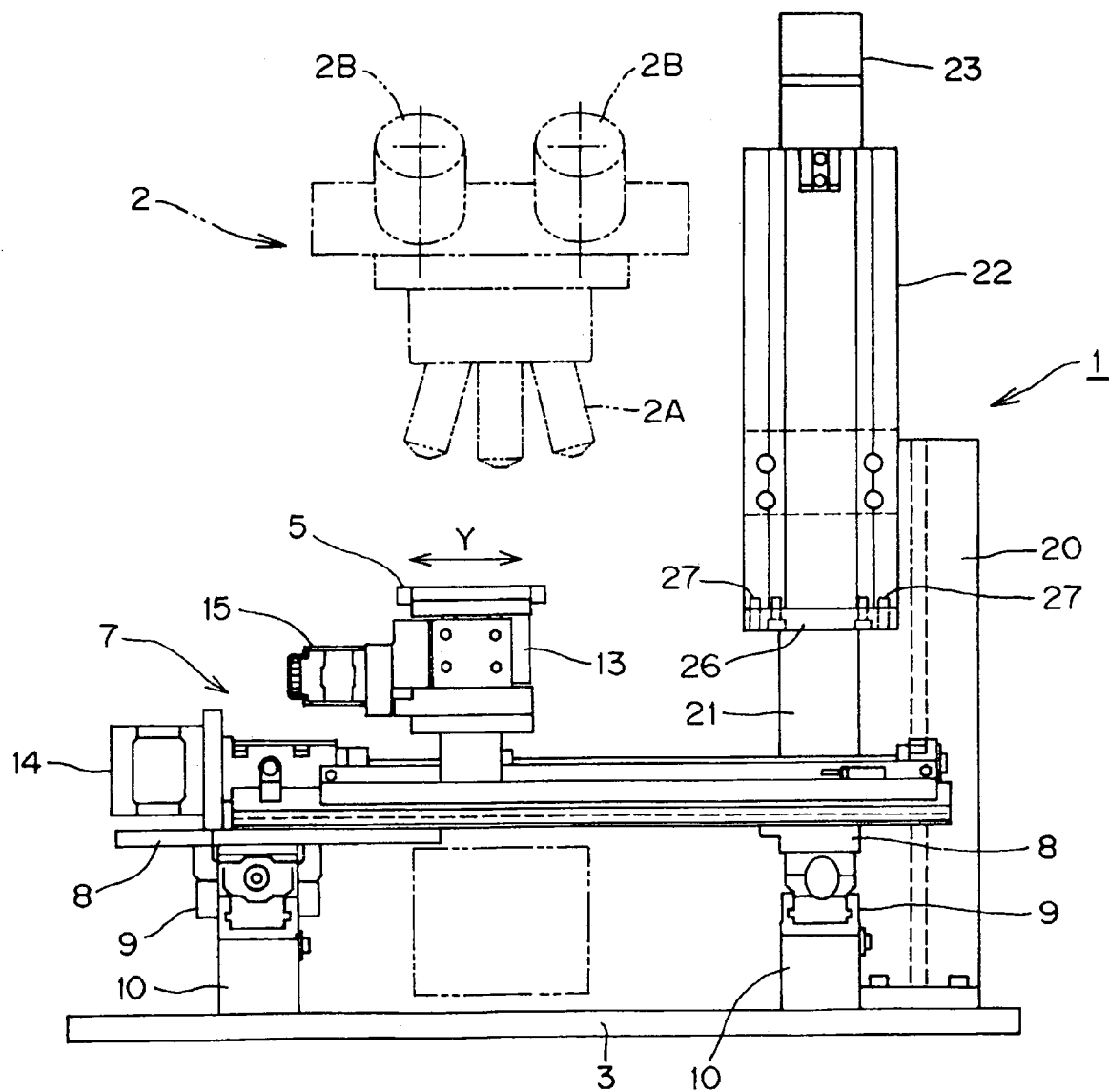
FIG. 2 is a front view showing the structure of the preparate photography system of the present invention.
Figure 3:
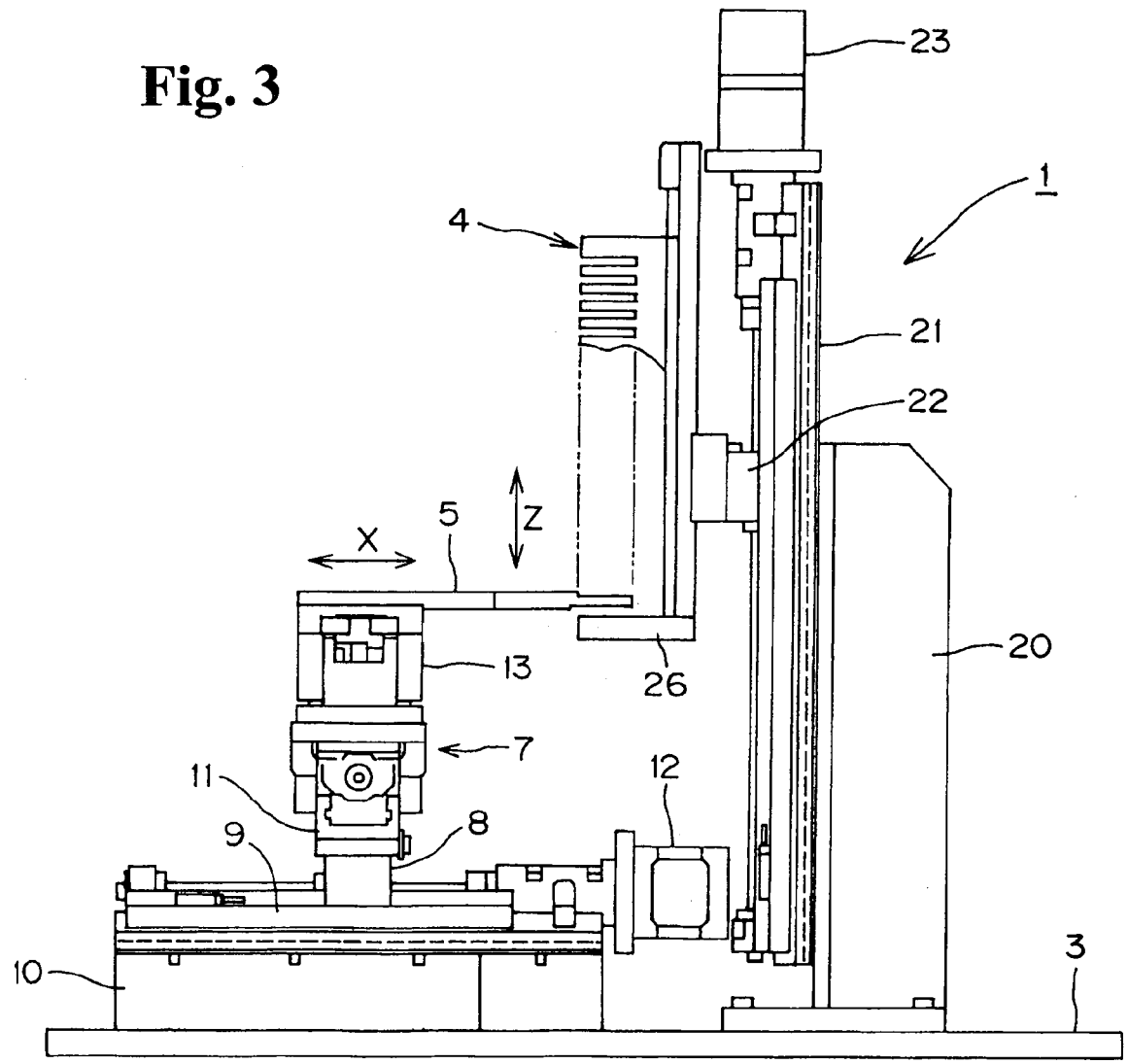
FIG. 3 is a side view showing the structure of the preparate photography system of the present invention.

FIG. 1 is a perspective view of the preparate photography system according to the present invention. FIG. 2 is a front view of the system, FIG. 3 is a side view of the system, and FIG. 4 is a plan view of the system.

The preparate photography system 1 of the present invention has a stand 3 on which a microscope 2 is mounted, and the system automatically performs the actions of removing a preparate stored in a preparate storage magazine 4 placed on the stand 3. However, only FIG. 2 shows a state in which the preparate was removed with a preparate holding hand 5, moving it between an object lens 2A of a microscope 2 and a condenser lens beneath that, or beneath a digital camera (81, not shown in FIGS. 1-4) provided separately from the microscope 2, and also returning it to the original preparate storage magazine 4.

The microscope 2 mounted on the preparate photography system 1 has a binocular eyepiece 2B for observing samples with the naked eye, and has internally a microscope camera. Photographs of samples are taken into the computer as digital data, and the picture data is compiled into a database for display on a display connected to the computer.

Figure 4:
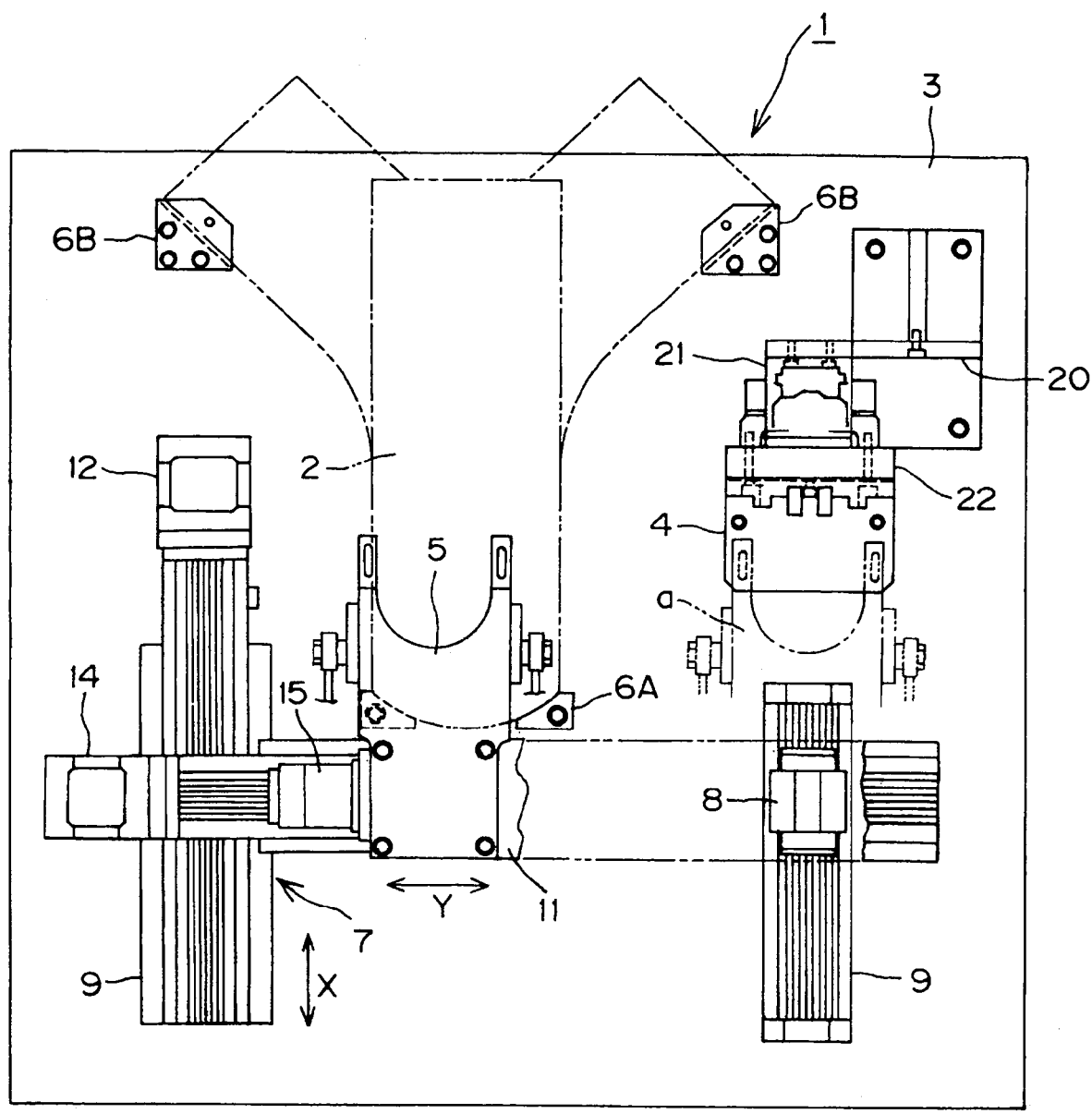
FIG. 4 is a plan view showing the structure of the preparate photography system of the present invention.

The microscope 2 is made to be attached to a prescribed position on the stand 3 by one fixing attachment 6A and two fixing attachments 6B which are attached on the stand 3 shown in FIG. 4. The fixing attachments 6A and 6B are fabricated to shapes matching the outline shapes of the leg parts of the microscope 2, and plural types of attachments having different shapes so as to be able to match microscopes of plural manufacturers, are prepared.

The preparate holding hand 5 is provided so as to be capable of moving on the stand 3 in the front-back direction (X direction in the drawing), left-right direction (Y direction in the drawing), and the up-down direction (Z direction in the drawing) by a three-dimensional movement mechanism 7. The three-dimensional movement mechanism 7 has a guide frame 9 (first guide member) which guides a movable frame 8 (first movable body) in order to move and position the preparate holding hand 5 in the front-back direction (X) of the stand 3.

In this embodiment, a pair of guide frames 9 is provided in parallel left and right on the stand 3 by means of spacers 10 with the respective longitudinal directions facing the front-back direction of the stand 3. The spacers 10 are exchangeable with plural types having different heights, and are prepared so as to match the specifications of microscopes of plural manufacturers.

A linear bearing is built into each guide frame 9, and is capable of displacing the movable frame 8 to slide smoothly following the longitudinal direction of the guide frame 9. Also, a guide frame 11 (second guide member) is fixed across the left and right pair of movable frames 8 which are moved by these guide frames 9, and it is made such that these movable frames 8 and the guide frame 11 can move as one in the front-back direction of the stand 3.

On one of these guide frames 9, a step motor 12 (first drive source) is attached on one end. This step motor 12 is drive-coupled to the movable frame 8 guided by the guide frame 9 to which it is attached, by means of a ball screw mechanism (not illustrated), which is built into the guide frame 9. By rotationally driving the drive shaft of the step motor 12 in the forward direction or reverse direction, this movable frame 8 moves horizontally in the front-back direction of the stand 3 following the guide frame 9. As a result, the guide frame 11 and the other movable frame 8, along with this movable frame 8, move as one in the front-back direction.

A linear bearing of the same kind as the one provided inside the guide frame 9 is built into the guide frame 11, and is capable of displacing a movable frame 13 (second movable body) to slide following the longitudinal direction of the guide frame 11.

Also, a step motor 14 (second drive source) of the same kind as the step motor 12 is attached on one end of the guide frame 11. The step motor 14 is drive-coupled to the movable frame 13 (second movable body) by means of a ball screw mechanism (also not illustrated), which is built into the guide frame 11 to which it is attached. By rotationally driving the drive shaft of the step motor 14 in the forward direction or reverse direction, the movable frame 13 moves horizontally in the left-right direction of the stand 3, following the guide frame 11.

On the top of the movable frame 13, the preparate holding hand 5 is attached to freely ascend and descend. The preparate holding hand 5 is drive-coupled with a step motor 15 (third drive source) attached to the movable frame 13, by means of a ball screw mechanism (not illustrated), as well as a linear cam mechanism, which are built into the movable frame 13. By rotationally driving the drive shaft of the step motor 15 in the forward direction or reverse direction, the preparate holding hand 5 moves in an ascending and descending manner with a horizontal posture on the movable frame 13 in linkage with the rotation.

Figure 5:
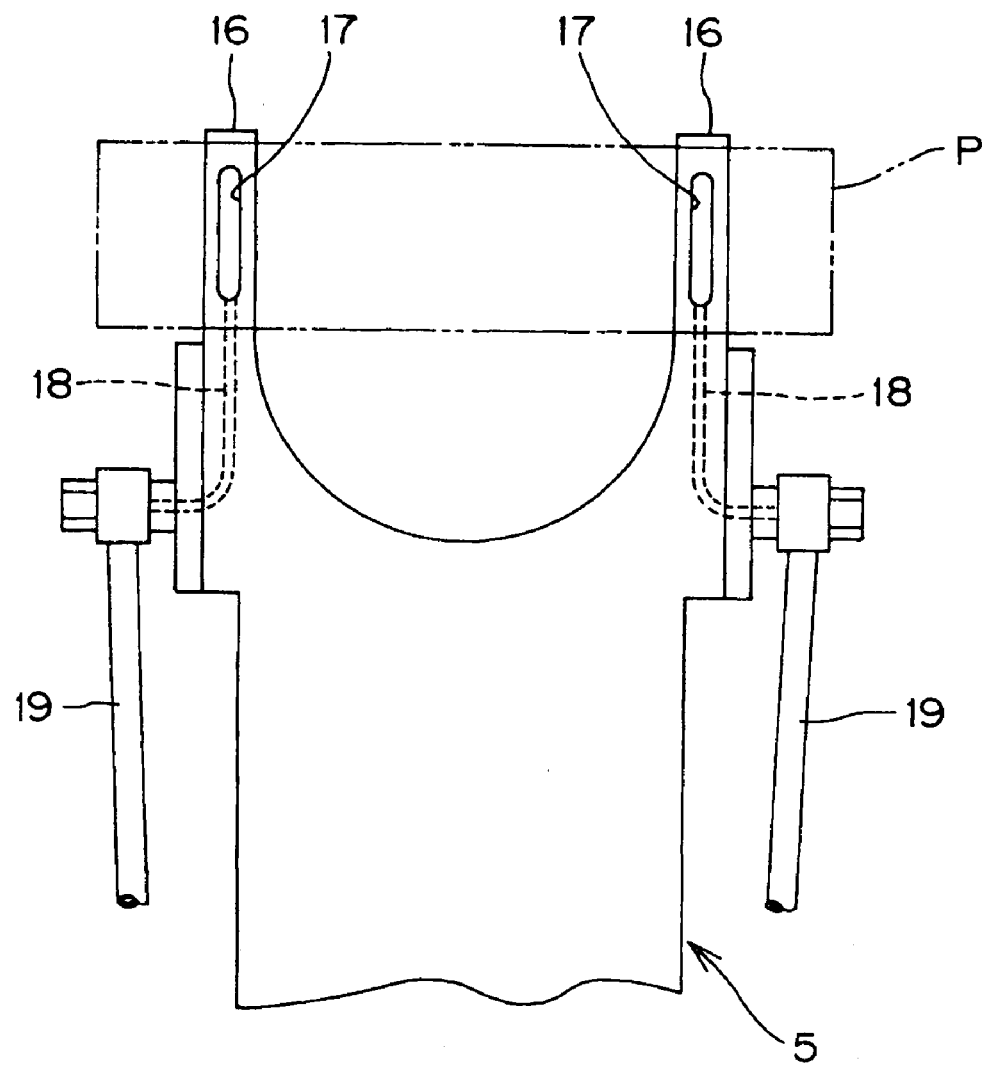
FIG. 5 is a plan view showing the structure of a preparate holding hand in the preparate photography system of the present invention.

As shown in FIG. 5, the preparate holding hand 5 has a pair of finger parts 16 for holding by mounting two ends of a preparate P containing a sample. Suction holes 17 are located respectively in the flat-finished upper surfaces of the finger parts 16.

The suction holes 17 communicate with a negative pressure (i.e., vacuum) source (not illustrated), by means of ventilation channels 18 formed inside the finger parts 16, a pair of ventilation tubes 19 connected to the two outsides of the bases of the finger parts 16, and a suction hose T shown in FIG. 1. The suction holes 17 are provided such that a preparate P adheres to the upper surfaces of the finger parts 16 by virtue of the negative pressure exerted on the suction holes 17 from the negative pressure source.

In the first embodiment of the invention, as shown in FIG. 1, a freely bendable cable guide L enables the suction hose T communicating with the ventilation tubes 19, and a power supply/control cable CB connected to the step motor 15 provided on the movable frame 13, to smoothly follow the movement of the movable frame 13 following the guide frame 11. The cable guide L is depicted only in FIG. 1.

Meanwhile, a support frame 20 is fixed on the upper surface of the stand 3 in a position to the side of the microscope 2, and a guide frame 21 (third guide member) is attached to this support frame 20. A linear bearing is built into the guide frame 21, and it supports and guides a movable frame 22 (third movable body) to be displaceable to ascend and descend following the longitudinal direction of the guide frame 21.

Also, a step motor 23 (fourth drive source) is provided on the upper end of the guide frame 21. The step motor 23 is drive-coupled to the movable frame 22 guided by the guide frame 21, by means of a ball screw mechanism (not illustrated), which is built into this guide frame 21. By rotationally driving the drive shaft of the step motor 23 in the forward direction or reverse direction, the movable frame 22 ascends and descends following the guide frame 21.

Figure 6:
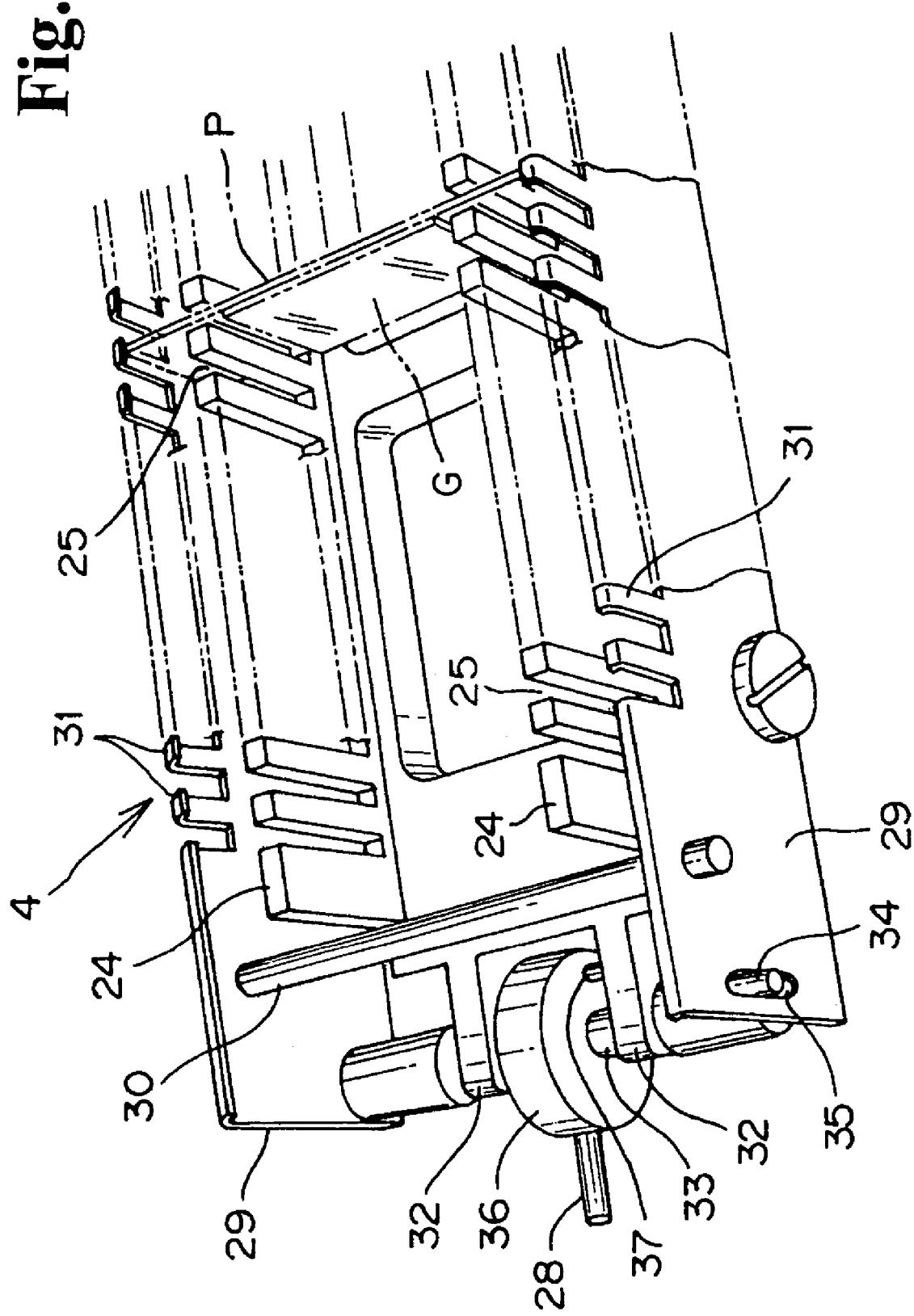
FIG. 6 is a partial perspective view of a preparate storage magazine in the preparate photography system of the present invention.

The system is configured such that the preparate storage magazine 4 can be installed to be freely attached to and detached from the front face of the movable frame 22. As shown in FIG. 6, the preparate storage magazine 4 has a pair of side wall plates 24 having plural preparate holding slots 25 arranged in parallel vertically for holding two ends of a preparate P sandwiching a sample between cover glass G. The magazine is configured so as to facilitate the insertion and removal of the preparates. The system is capable of receiving plural preparates P arranged vertically in a shelf-like manner at an interval such that the finger parts 16 of the preparate holding hand 5 can be inserted and removed.

Figure 7:
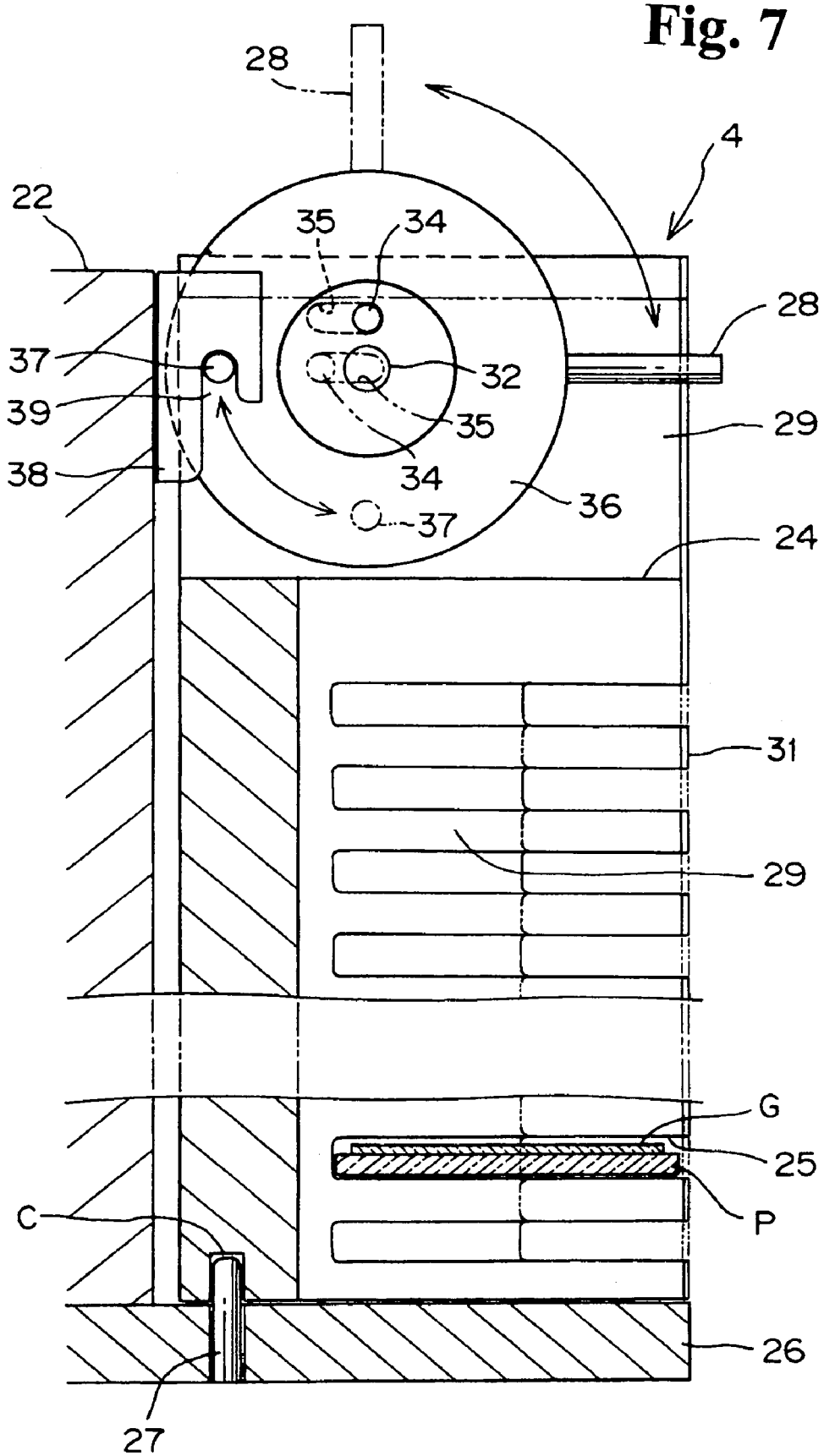
FIG. 7 is a sectional view showing an internal structure of the preparate storage magazine in the preparate photography system of the present invention.

As shown in FIG. 7, a support plate 26 for carrying the preparate storage magazine 4 is attached to the lower end of the movable frame 22 in order to fix the preparate storage magazine 4 to the side of the movable frame 22. Support plate 26 is made such that the preparate storage magazine 4 is fixed to the movable frame 22 when a pair of left and right positioning pins 27 placed protruding on the upper surface of this support plate 26 are inserted into positioning holes C provided on the lower end surfaces of the preparate storage magazine 4, and when an attachment/detachment lever 28 provided on the upper end of the preparate storage magazine 4 is rotated to the locked position shown by the solid line in FIG. 7.

As shown in FIG. 6, a pair of movable stoppers 29 is provided on both outsides of the two side wall plates 24 on the left and right sides of the preparate storage magazine 4. These movable stoppers 29 are formed in plate shape parallel to the side wall plates 24, and they are mutually coupled so as to become a pair left and right by a coupling rod 30. The movable stoppers 29 are made capable of relative displacement in the longitudinal direction against the pair of side wall plates 24 by half the distance of the arrangement pitch of the preparate holding slots 25.

The movable stoppers 29 have comb tooth-shaped stopper pieces 31 which are formed at the same pitch as the interval of the preparate holding grooves 25 provided on the left and right side plate parts 24. The tips of these stopper pieces 31 are bent into hook shapes turning inward. As shown in FIG. 6, when these hook-shaped tips are in a position facing opposite the preparate holding slots 25 of the side wall plates 24, the preparates P held in the preparate holding slots 25 of the pair of side wall plates 24 are prevented from slipping out forward from the preparate holding slots 25.

Also, the depth of the slits formed between the comb tooth-shaped stopper pieces 31 of the movable stoppers 29 is formed so as to be less than the front-back width of the preparate P. Any possible slipping-out of the preparates P in the lateral direction from the preparate holding slots 25 is restricted by the inner wall surfaces of the movable stoppers 29 on the two sides.

Meanwhile, when the movable stoppers 29 are displaced in the longitudinal direction of the side wall plates 24, and the hook-shaped tips of the stopper pieces 31 are shifted half pitch from the position facing opposite the preparate holding slots 25, it becomes possible to remove the preparates P from the preparate holding slots 25 without interference from the stopper pieces 31.

In the present embodiment, action of the movable stoppers 29 is performed in linkage with the rotation of the attachment/detachment lever 28. The rotating shaft 32 of the attachment/detachment lever 28 is supported to rotate freely by a shaft bearing part 33 which is integrally coupled with the pair of side wall plates 24 of the preparate housing magazine 4, and eccentric shafts 34 are provided respectively on both ends of this rotating shaft 32.

The eccentric shafts 34 respectively are inserted into long holes 35 formed on the left and right movable stoppers 29. When the attachment/detachment lever 28 is moved between the locked position shown by the solid line in FIG. 7 and the unlocked position shown by the broken line, the left and right movable stoppers 29 are displaced in the longitudinal direction of the side wall plates 24 by means of these eccentric shafts 34.

Meanwhile, the attachment/detachment lever 28 is fixed on the outer perimeter surface of a cylindrical part 36 provided on the rotating shaft 32, and lock pins 37 are provided on both the left and right sides of this cylindrical part 36. When the preparate storage magazine 4 is attached to the movable frame 22 and the attachment/detachment lever 28 is rotated to the locked position, the lock pin 37 couples in a lock pin coupling slot 39 of a coupling piece 38 fixed on the side of the movable frame 22 as shown by the solid line in FIG. 7. In joint operation with the positioning pin 27, the preparate storage magazine 4 is therefore fixed to the movable frame 22. When the attachment/detachment lever 28 is in this locked position, the movable stopper 29 ascends to the position indicated by the solid line in the same drawing where the preparates P can be inserted and removed.

Next, the operation and action of the preparate photography system 1 of the present invention are explained. First, the preparate storage magazine 4 is removed from the movable frame 22, and the attachment/detachment lever 28 is rotated to the locked position, and in that condition, preparates P containing samples are inserted into the opposing preparate holding slots 25 of the pair of side wall plates 24.

A maximum of 20 preparates P can be stored. When the operation of storing the preparates P in the preparate storage magazine 4 is completed, the attachment/detachment lever 28 is rotated to the unlocked position, and the preparates P are prevented from falling out during carrying of the preparate storage magazine 4.

Next, preparate storage magazine 4 is installed on the movable frame 22 of the preparate photography system 1. For installation, first, the positioning pins provided on the support plate 26 of the movable frame 22 are inserted into the positioning holes on the bottom surface of the preparate storage magazine 4, after which the attachment/detachment lever 28 is rotated to the locked position, and the microscope 2 is fixed to the movable frame 22.

Meanwhile, the preparate holding hand 5 at the start of the process is in the waiting position in front of the preparate storage magazine 4 indicated by symbol a in FIG. 4. Also, the preparate holding hand 5 is in a position having gone down to the lower limit on the movable frame 13. Meanwhile, the movable frame 22 is stopped at a position having ascended to a reference position near the upper limit position on the guide frame 21.

From this state, the step motor 12 is driven, the guide frame 11 moves forward toward the side of the preparate storage magazine 4, and accompanying this, the pair of finger parts 16 provided on the preparate holding hand 5 enters beneath the preparate P in the lowest position in the preparate storage magazine 4 held on the movable frame 22. Here, the step motor 12 stops, and the suction holes 17 provided on the respective finger parts 16 are positioned so as to come directly beneath said preparate P.

Next, the step motor 23 is driven and the preparate storage magazine 4 descends slightly, and the preparate P having both ends held on the upper surfaces of the preparate holding slots 25 of the left and right side wall plates 24 of the preparate storage magazine 4 is transferred to the pair of finger parts 16. At the same time, negative pressure is applied to the suction holes 17 of the finger part 16 from the negative pressure source (not illustrated), and the preparate P is drawn by suction and fixed to the upper surfaces of the finger parts 16.

Next, the step motor 12 is driven in the reverse direction, and the preparate holding hand 5 is retracted to position a in FIG. 4 together with the guide frame 11. Then, the step motor 14 is driven and the movable frame 13 is moved following the guide frame 11, and the preparate holding hand 5 is made to face opposite the front face of the microscope 2. From here, the step motor 12 is driven and the preparate holding hand 5 is driven to advance toward the microscope 2 together with the guide frame 11. The motor is stopped such that the preparate P adhered to the pair of finger parts 16 comes directly beneath the object lens 2A of the microscope 2.

Here, photography of the sample contained in the preparate P is performed by the microscope camera provided in the microscope 2, and picture data is input to the computer. At this time, examination and observation of the sample can be performed also by the naked eye through the eyepiece 2B of the microscope 2.

Here, focal adjustment of the sample is performed automatically by drive-controlling the step motor 15 using an autofocus function to be described later, and adjusting the position of the preparate holding hand 5 in the vertical direction. Also, in the case of adjusting and scanning the position of the sample with respect to the object lens 2A, it is performed by respectively drive-controlling the step motor 12 and the step motor 14.

When photography of the sample is completed, the step motor 15 is driven, and the preparate holding hand 5 descends to the lower limit position on the movable frame 13. Next, the step motor 12 is driven in the reverse direction and the preparate holding hand 5 is retracted together with the guide frame 11. The step motor 14 is also driven, whereby the preparate holding hand 5 moves to the waiting position a following the guide frame 11.

When the preparate holding hand 5 reaches the waiting position a, the step motor 12 is driven in the forward direction and the preparate holding hand 5 again moves toward the preparate storage magazine 4. The preparate P held on the finger parts 16 is returned to the original position on the preparate storage magazine 4.

Here, the negative pressure acting on the suction holes 17 of the finger parts 16 is released. Next, the step motor 23 is driven and the preparate storage magazine 4 ascends slightly, and the preparate P held on the pair of finger parts 16 is held in the preparate holding slots 25 of the preparate storage magazine 4 where it was originally located. After that, the preparate holding hand 5 is retracted by driving the step motor 12 in the reverse direction, and the preparate holding hand 5 stops at the waiting position a.

Also, when continuing to supply other preparates P to the microscope 2, the step motor 23 is driven and the movable frame 22 descends by one pitch worth of the preparate holding slots 25 of the preparate storage magazine 4 on the guide frame 21, and then the same series of actions as described above is repeated.

The series of actions described above is performed automatically by program control by a computer to be described later. Also, if it is desired to supply the preparates P stored in the preparate storage magazine 4 to the microscope 2 in an arbitrary order, the series is performed by inputting that order into the computer manually.

The first embodiment of the invention is configured such that the preparate storage magazine 4 is attached to and detached from the movable frame 22. In another possible embodiment of the invention, it may be a configuration in which the preparate storage magazine 4 is not removable from the movable frame 22. In such an embodiment, because there is no fear that the preparates P may fall from the preparate storage magazine 4 and be broken, the configuration can be simplified by not incorporating the movable stoppers 29 in the preparate storage magazine 4.

Also, in the first embodiment, a step motor was used as a drive source for the three-dimensional movement mechanism of the preparate holding hand 5, and it was configured such that the rotation caused each movable frame (movable body) to move by means of a ball screw mechanism. But, the present invention is not necessarily limited to such a structure. For example, a direct current servo motor or an ultrasonic motor may be used as the drive source. It also may be configured such that the movable frame is driven directly by incorporating a linear step motor in the guide frame (guide member) without interposing a power transmission mechanism.

Also, in the first embodiment, the suction holes 17 are located respectively in the pair of finger parts 16 of the preparate holding hand 5. In another possible embodiment of the invention, the preparate holding hand 5 may be configured such that a suction hole is provided in only one finger part, and the other finger part simply supports the preparate.

Figure 8:
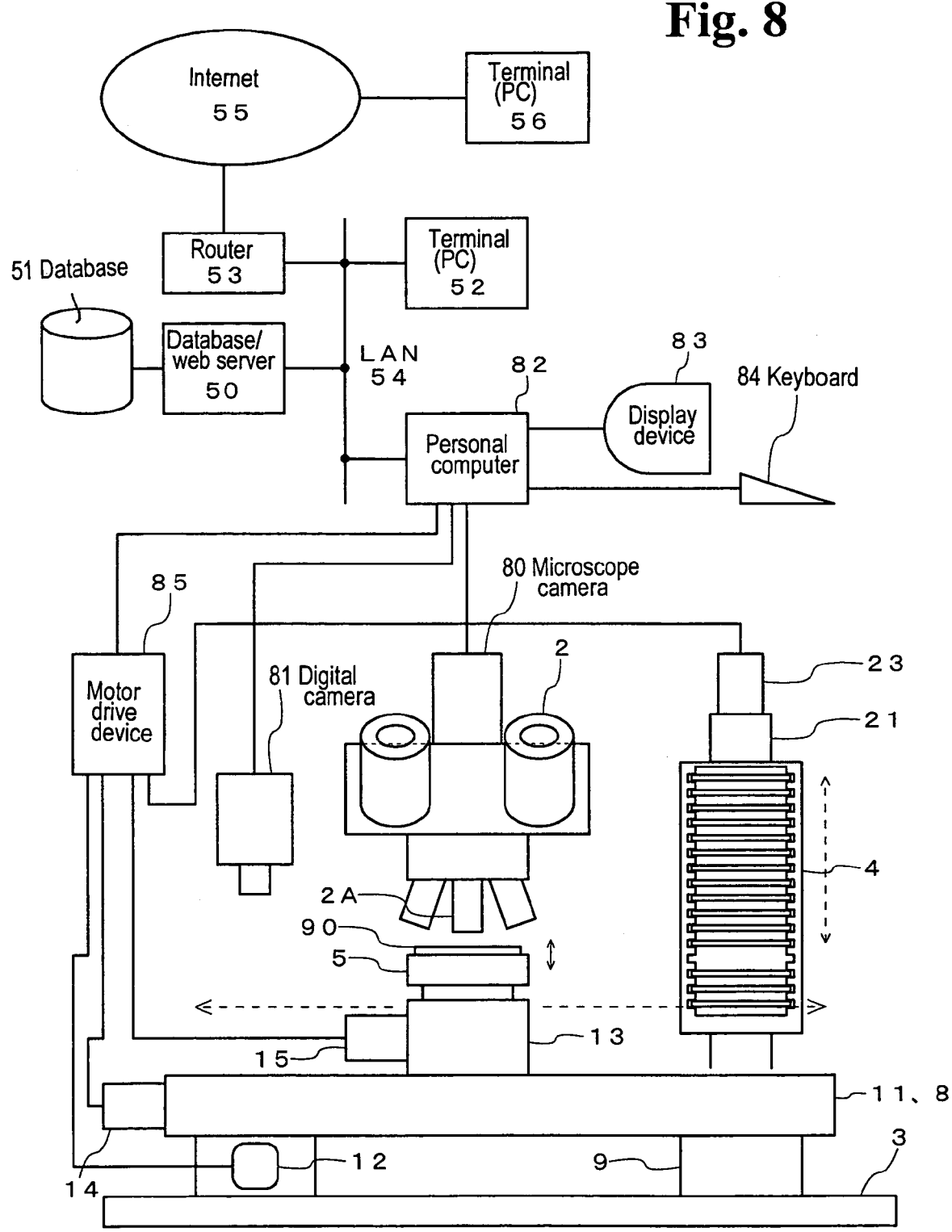
FIG. 8 is a block diagram showing the overall configuration of a system including a slide picture data creation system of the present invention.

Next, the control processing functions are explained. FIG. 8 is a block drawing showing the overall configuration of a system including the slide picture data creation system according to the present invention. The system generally includes the aforementioned preparate photography system including a microscope 2, and a personal computer 82 for control and image processing. Also, the personal computer 82 is connected with a database/web server 50, a database 51, and a terminal (PC) 52 via a LAN 54. Furthermore, the database/web server 50 is connected to an external terminal (PC) 56 via a router 53 and the Internet 55.

The personal computer 82 is a standard personal computer having standard hardware, and is connected with a display device 83, keyboard 84, mouse, LAN 54, and the like. Also, the personal computer 82 is connected with a microscope camera 80, digital camera 81, motor drive device 85, and the like, by, for example, a USB interface. The personal computer 82 executes the processing described below based on operating instructions from a user.

Figure 10:
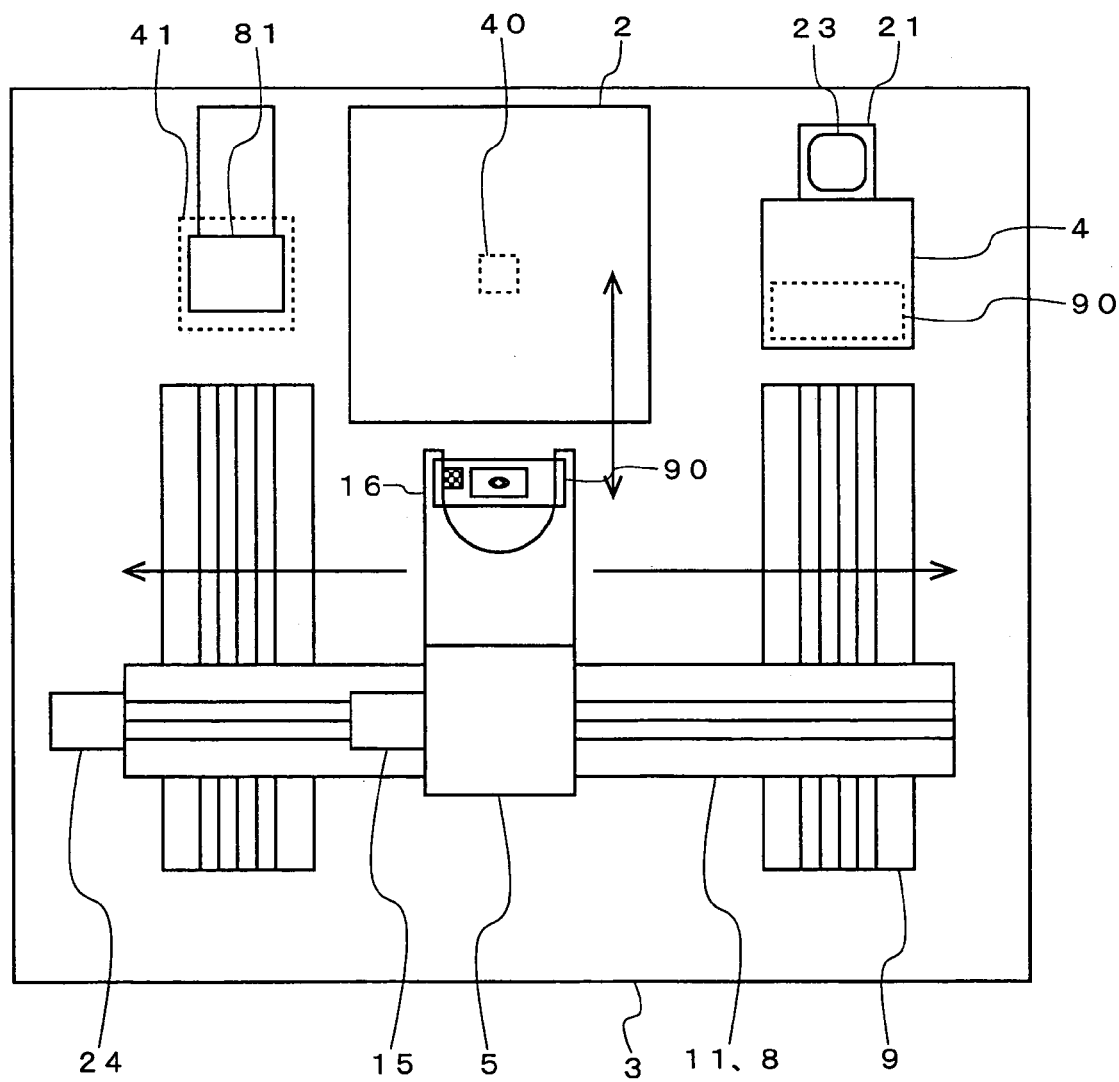
FIG. 10 is a plan view showing the configuration of the preparate photography system of the present invention.

FIG. 10 is a plan view showing the configuration of the preparate photography system. The preparate photography system, as described above, includes a microscope 2 fixed on a stand 3, and a digital (external) camera 81, a drive device 21 of the preparate storage magazine 4, a three-dimensional movement mechanism 7 for holding and moving preparates, and a motor drive device 85.

The microscope 2 internally has a digital microscope camera 80 that can be controlled by the personal computer 82, and high-magnification pictures of samples photographed by the microscope camera 80 are taken into the personal computer 82 as digital data.

The digital (external) camera 81 is fixed on the stand 3, and it outputs ordinary camera still picture data to the personal computer 82 based on control from the personal computer 82. The digital camera 81 is used for photography of loupe pictures, which are overall pictures of the sample portions of preparates 90, and for the recording of two-dimensional bar codes 42, and the like.

The three-dimensional movement mechanism 7, as previously described, includes a first movable frame 8 which is capable of movement in the front-back direction, a second movable frame 13 which is capable of movement in the left-right direction, and a preparate holding hand 5 which is capable of moving in the up-d down direction. Also, mechanism 7 is configured such that preparates 90 are held by the preparate holding hand 5 and can be moved to any position in the front-back, left-right, and up-down directions by driving of each step motor by the motor drive device 85 based on control from the personal computer 82.

The three-dimensional movement mechanism 7 automatically performs the actions of removing preparates 90 from the preparate storage magazine 4, moving them beneath the digital camera 81 and between the object lens 2A and condenser lens (not illustrated) of the microscope 2, and returning them to the preparate storage magazine 4.

In the photography of high-magnification pictures, because one sample must be photographed by being divided into a large number of pictures, the positions in the front-back and left-right directions to be photographed are adjusted. Also, plural pictures are photographed while moving the preparate holding hand 5 by minute lengths over a prescribed range in the up-down direction centered on the focused position. The movable range of the up-down movement is made within 2 millimeters so that collision with the object lens 2A does not occur, and adjustment of the focus is performed within that range.

Figure 11:
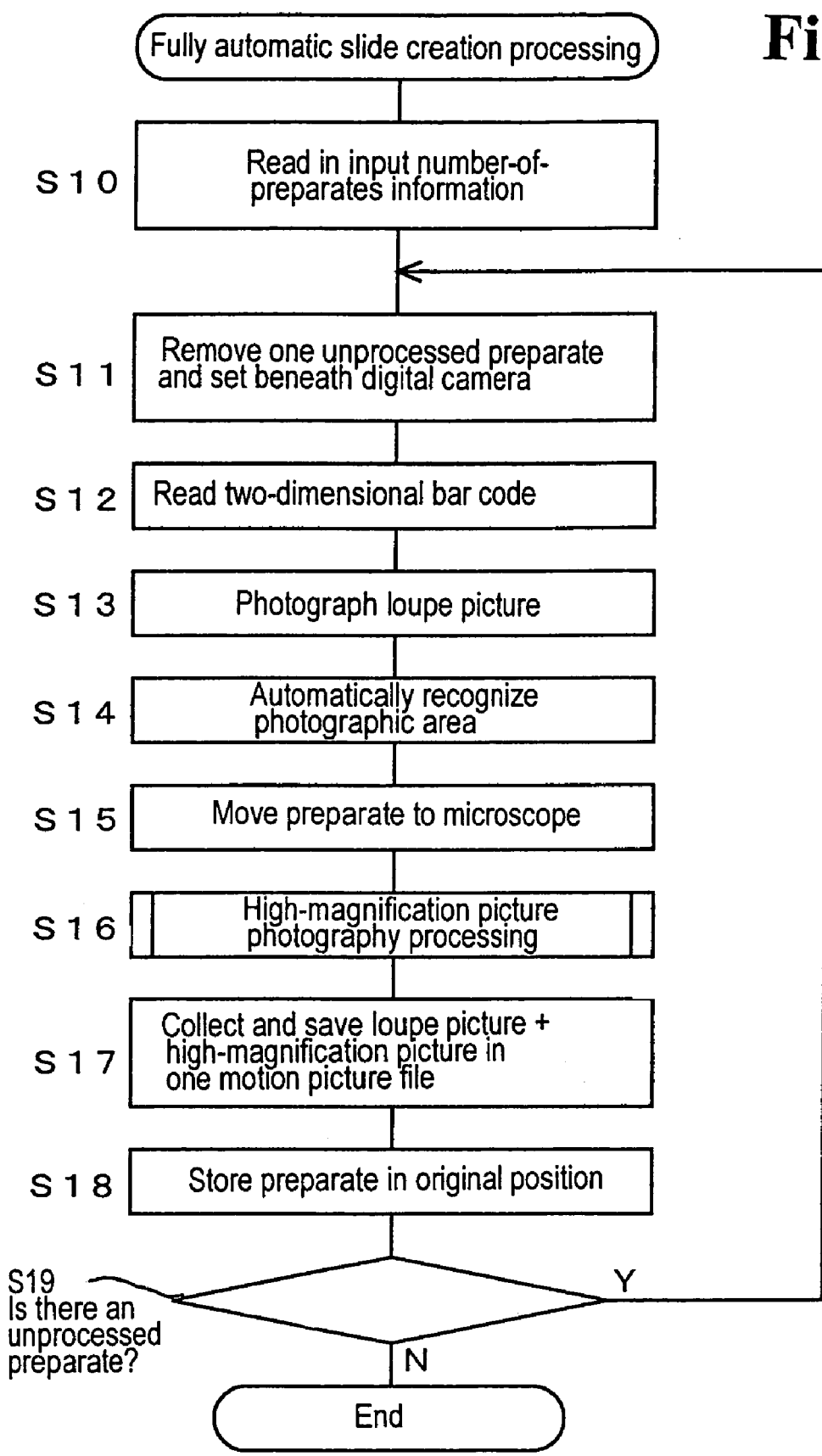
FIG. 11 is a flow chart showing the steps associated with fully automatic slide creation processing according to the present invention.

FIG. 11 is a flow chart showing the steps associated with fully automatic slide creation processing according to the present invention. The processing is executed by the personal computer 82. In this processing, the preparates to be photographed are first set in the preparate storage magazine 4 by being loaded from the bottom up. In S10, the number-of-preparates information input by the user is read in. In S11, the three-dimensional movement mechanism 7 is controlled and one unprocessed preparate is removed and is placed beneath the digital camera 81.

Figure 9:
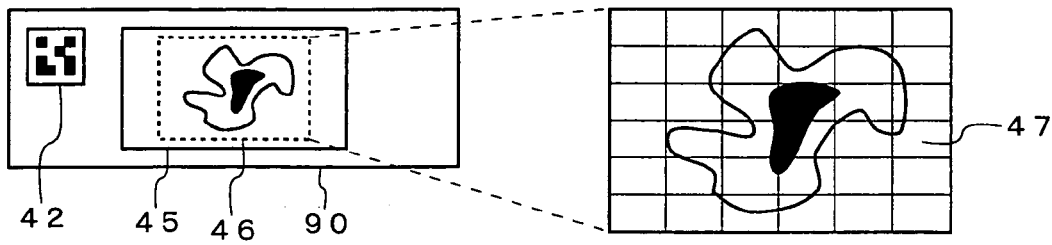
FIG. 9 is a plan view showing an example of a preparate used in the present invention.

FIG. 9 is a plan view showing an example of a preparate used in the present invention. A sample is sandwiched between the slide glass and the cover glass 45 of the preparate 90. On the upper left corner of the preparate 90, a two-dimensional bar code 42, such as, for example, a QR code recording the identification number of the preparate, is affixed. In S12, the two-dimensional bar code 42 is read using the digital camera 81.

In S13, a loupe picture is photographed using the digital camera 81. A loupe picture is a picture of the scope indicated by the dotted line 46 in FIG. 9, and it includes all the areas of the sample. An enlarged version of the loupe picture is depicted on the right side of FIG. 9.

In S14, the photographic area of the high-magnification picture is automatically recognized. Because the photographic area of a high-magnification microscope camera 80 is narrow, the entirety of the area of the sample cannot be photographed in one picture. Therefore, as shown on the right side in FIG. 9, the loupe picture is divided into plural areas 47 in a matrix pattern (e.g., 6×6 in FIG. 9). Areas slightly wider than the respective divided areas 47 are photographed by the high-magnification microscope camera 80.

Also, when the sample tissue is scattered on the preparate, photography of marked areas in which only the necessary parts have been automatically extracted is performed for the purpose of speeding up processing and reducing file capacity. For example, when it is recognized by picture processing that there is no sample in the divided pictures in the left column in the drawing on the right side of FIG. 9, photography of the left column is not performed. Or, it may be made such that only the area having the sample is extracted from the loupe picture, and only the scope covering the extracted area is photographed using the high-magnification microscope camera 80.

In S15, the three-dimensional movement mechanism 7 is controlled and the preparate 90 is moved beneath the object lens 2A of the microscope 2. In S16, high-magnification picture photography processing to be described later is performed. At this time, thumbnail pictures (i.e., reduced-size pictures of an entire picture) are generated by pasting together high-magnification pictures.

In S17, the loupe picture+thumbnail pictures+and high-magnification pictures are collected in one motion picture file, and it is registered and saved in the database 51 provided on the database/web server 50 together with the identification number of the preparate. In the database 51, it is assumed that other information such as the corresponding patient name is already registered corresponding to the identification number of the preparate.

Figure 15:
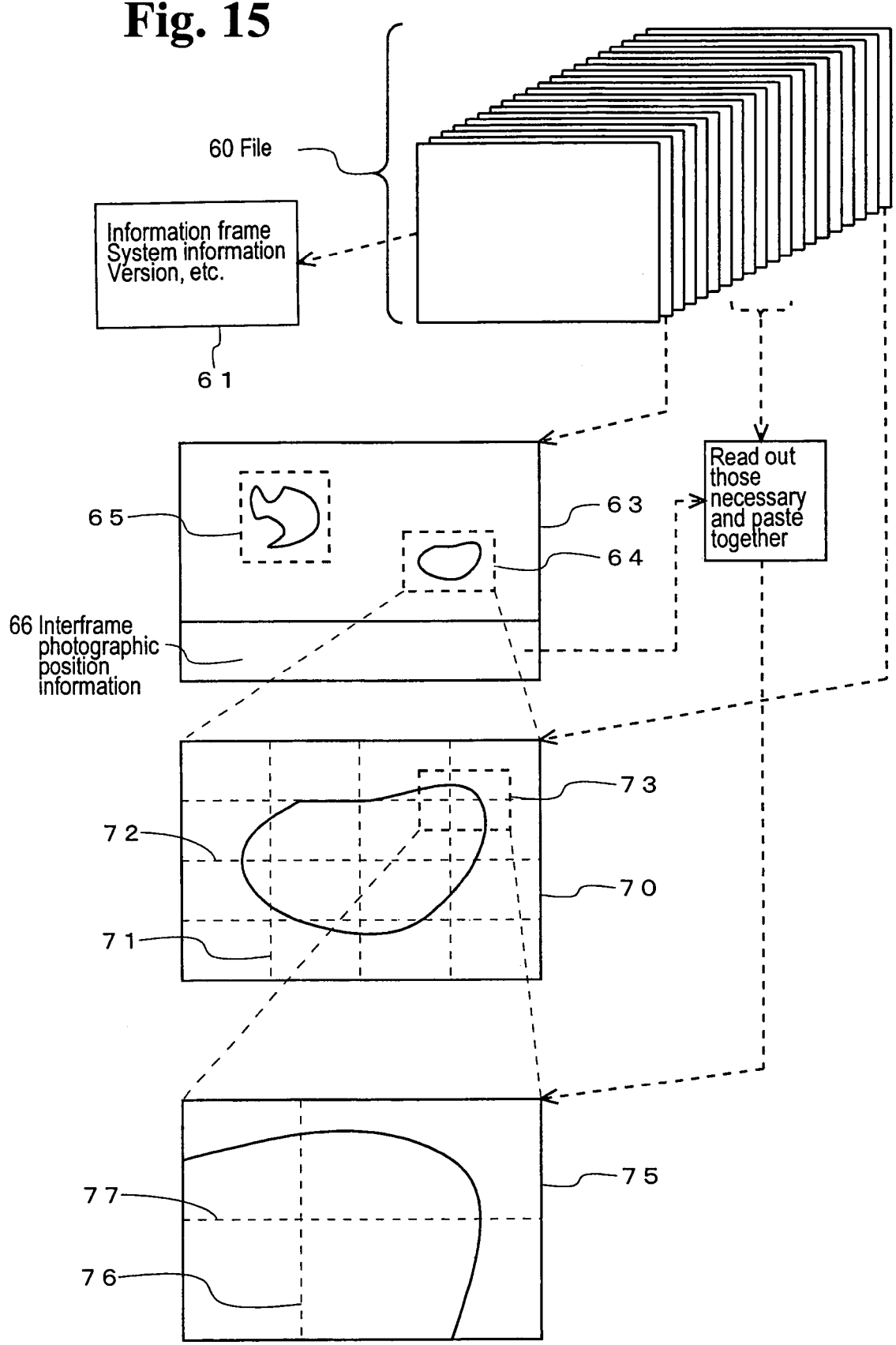
FIG. 15 is an explanatory diagram showing an example of a file structure and a picture that is displayed according to the present invention.

FIG. 15 is an explanatory drawing showing an example of a file structure and a picture that is displayed. The motion picture file 60 consists of plural frame data, and in the first frame, an information frame 61 is stored. In the information frame 61, information such as system information, machine name, version information, photographic magnification, system configuration, camera name, and the like, is stored. In the second frame, the loupe picture 63 is stored, and in this frame, interframe photographic position information also is stored. In the final frame, the thumbnail pictures 70 are stored, and in the third frame to the frame one before the final frame, the high-magnification pictures are stored.

Returning to FIG. 11, in S18, the three-dimensional movement mechanism 7 is controlled and the preparate is stored in the original position. In S19, it is determined as to whether or not there is an unprocessed preparate, and if the result of the determination is positive, it moves to S11, and if it is negative, the processing ends.

Figure 12:
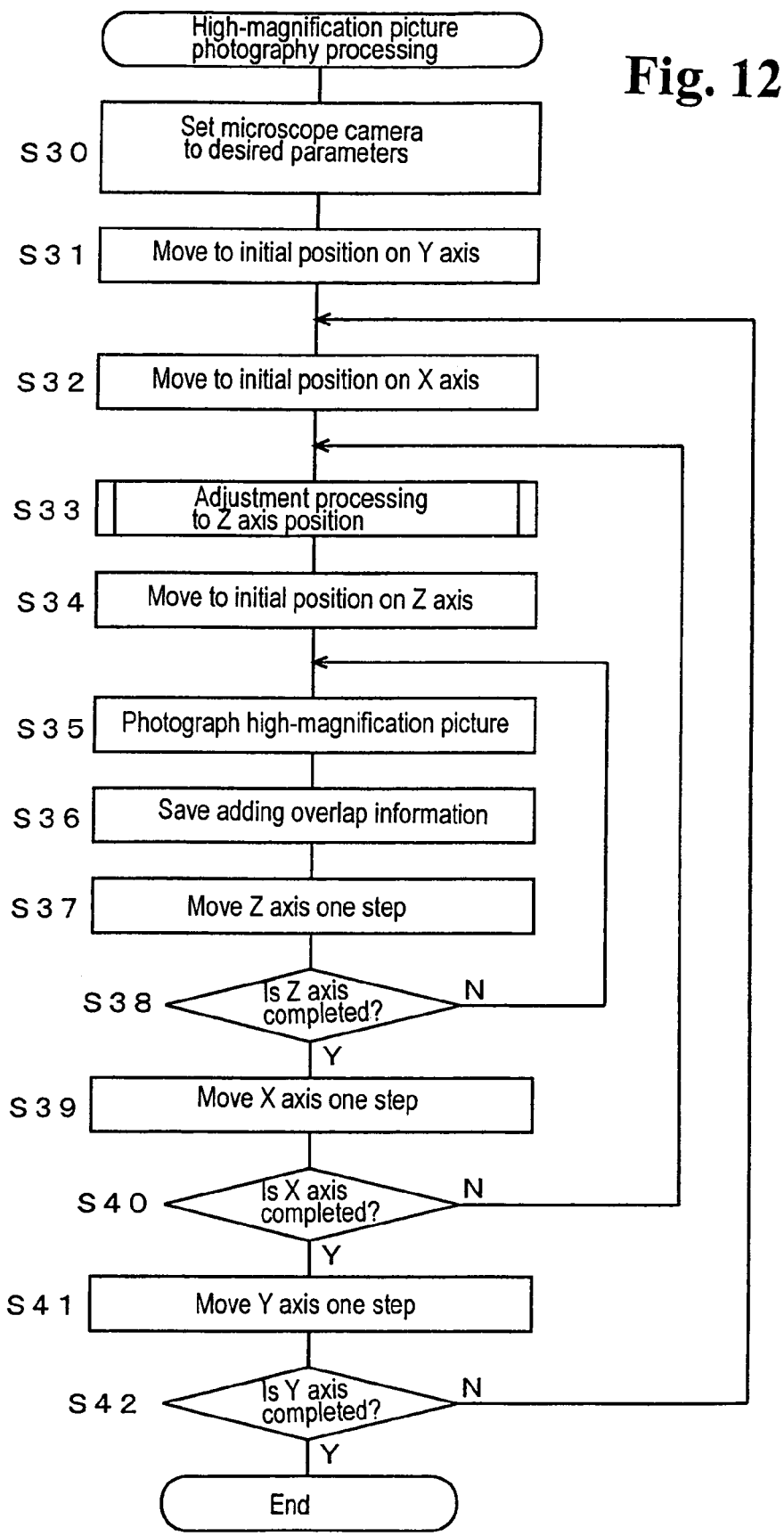
FIG. 12 is a flow chart showing the steps associated with high-magnification photography processing in S16.

FIG. 12 is a flow chart showing the substance of high-magnification picture photography processing in S16. In S30, the desired parameters for exposure time, shutter speed, color balance, and the like, are set in the microscope camera 80. In S31, camera 80 is moved to the initial position on the Y axis (left-right direction). For example, in the case of photographing the entire area of a loupe picture, the preparate 90 is moved to the position where the topmost row of divided pictures of the loupe picture enters into the photographic area of the microscope camera 80.

In S32, the preparate 90 is moved to the initial position on the X axis. For example, in the case of photographing the entire area of a loupe picture, the preparate 90 is moved to the position where the leftmost column of divided pictures of the loupe picture enters into the photographic area of the microscope camera 80. In S33, Z axis adjustment processing to be described later is performed, and the Z axis position of the focal point is detected.

In S34, the preparate 90 is moved to the initial position on the Z axis. In the present invention, in the Z axis direction, as many as 20 high-magnification pictures are photographed while changing the position at equal intervals over a prescribed range centered on the focal position. Accordingly, in S34, the preparate 90 is moved downward by a prescribed length from the focal position.

In S35, a high-magnification color picture is photographed by the microscope camera 80, and the picture data is read in. In S36, when there are other high-magnification pictures above and below, left and right (XY axis directions), overlap information with those pictures is generated. Overlap information is information indicating, for example, how many pixels are overlapped with the other pictures, i.e., a determination of which pixels are to be to pasted together. The overlap information is obtained, for example, by taking a correlation of the pictures on the edges while changing the number of pixels overlapped.

The obtained overlap information is saved and added to the picture data. The format of the saved file may be a picture file format, for example, based on JPEG2000. The overlap information takes a form to be incorporated into the high-magnification picture itself. As incorporated information, in addition to overlap information, system information such as AF (autofocus) information, hardware identification information and photographic software version information, X, Y, Z position information, and the like, are stored. The number of pixels of one high-magnification picture, for example, may be 1280×1024. Furthermore, at this time, thumbnail pictures of connected-together high-magnification pictures are generated.

In S37, the Z axis is moved one step. The width of one step may be, for example, 0.5 microns. In S38, it is determined as to whether or not the processing of the Z axis is completed by whether or not the Z axis has reached the final position. If the result of the determination is negative, the process moves to S35, and if the result is positive, the process moves to S39.

In S39, the X axis is moved one step. The width of one step changes according to the magnification being used. For example, at a magnification of 40 times, the width of one step is about 0.18 millimeters. In S40, it is determined as to whether or not the processing of the X axis is completed by whether or not the X axis has reached the final position. If the result of the determination is negative, the process moves to S35, and if the result is positive, the process moves to S39.

In S41, the Y axis is moved one step. In S42, it is determined as to whether or not the processing of the Y axis is completed by whether or not the Y axis has reached the final position. If the result of the determination is negative, the process moves to S35, and if the result is positive, the processing ends.

Figure 13:
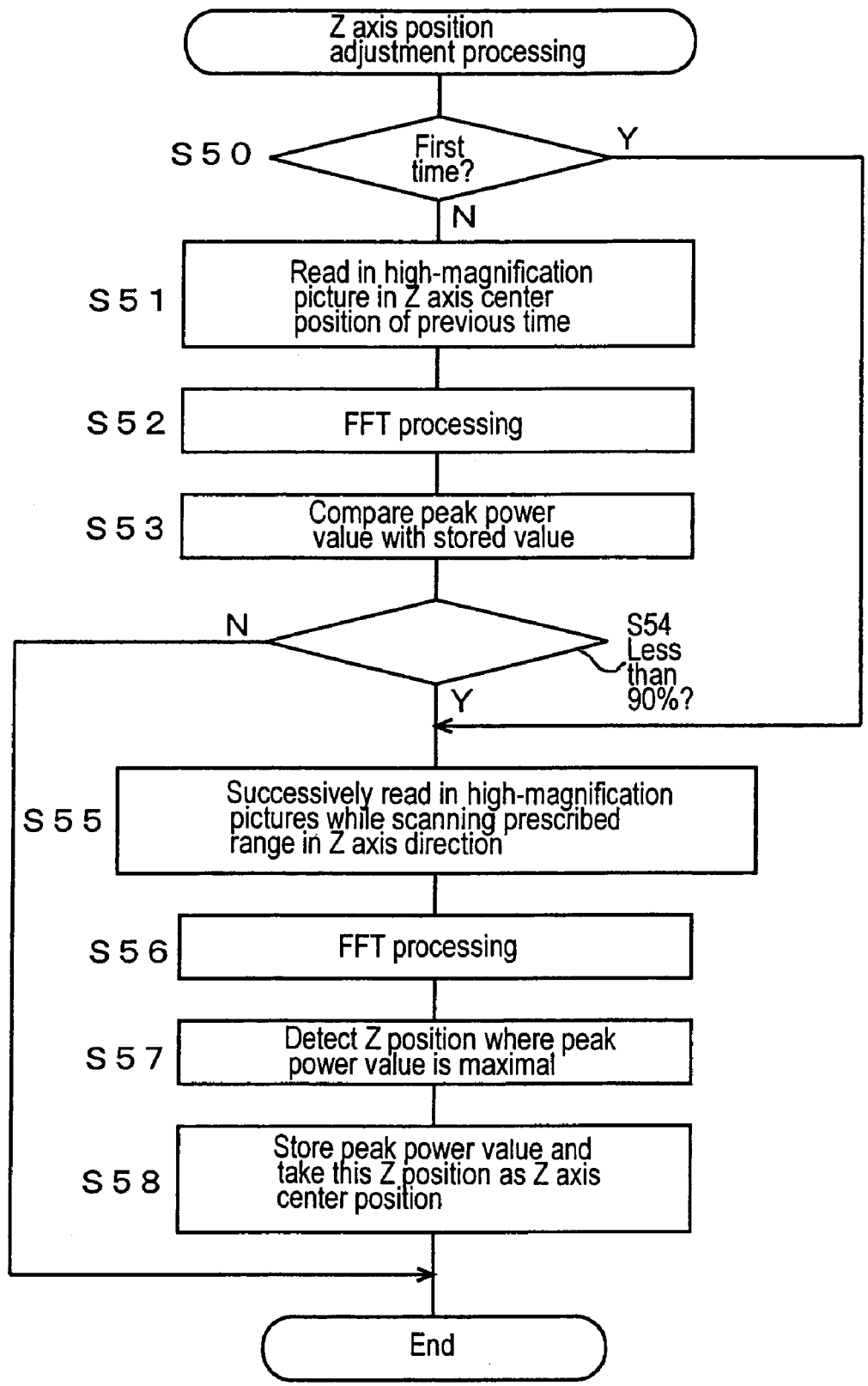
FIG. 13 is a flow chart showing the steps associated with Z axis position adjustment processing in S33.

FIG. 13 is a flow chart showing the steps associated with Z axis position adjustment processing in S33. In S50, it is determined as to whether or not execution of Z axis position adjustment processing is being done for the first time. If the result of the determination is negative, the process moves to S51, and if the result is positive, the process moves to S55.

In S51, a high-magnification picture is read in at the Z axis center position from the previous sequence. In S52, FFT (Fast Fourier Transform) processing is performed, and a frequency spectrum of the picture is computed.

In S53, the peak power value of the frequency spectrum is compared with a stored value. In S54, it is determined as to whether or not the peak power value is, for example, less than 90% of the stored value. If the result of the determination is negative, the Z axis position is not changed, and the focal position from the previous time is used, so processing ends. But, if the result is positive, the process moves to S55 and the focal position is recomputed.

In S55, high-magnification pictures are successively read in while scanning a prescribed range in the Z axis direction. In S56, FFT (Fast Fourier Transform) processing is performed for all of the pictures, and a frequency spectrum of the pictures is computed. In S57, the Z position where the peak power value is maximal is detected. In S58, the peak power value is stored, and this Z position is then taken as the Z axis center position.

Figure 14:
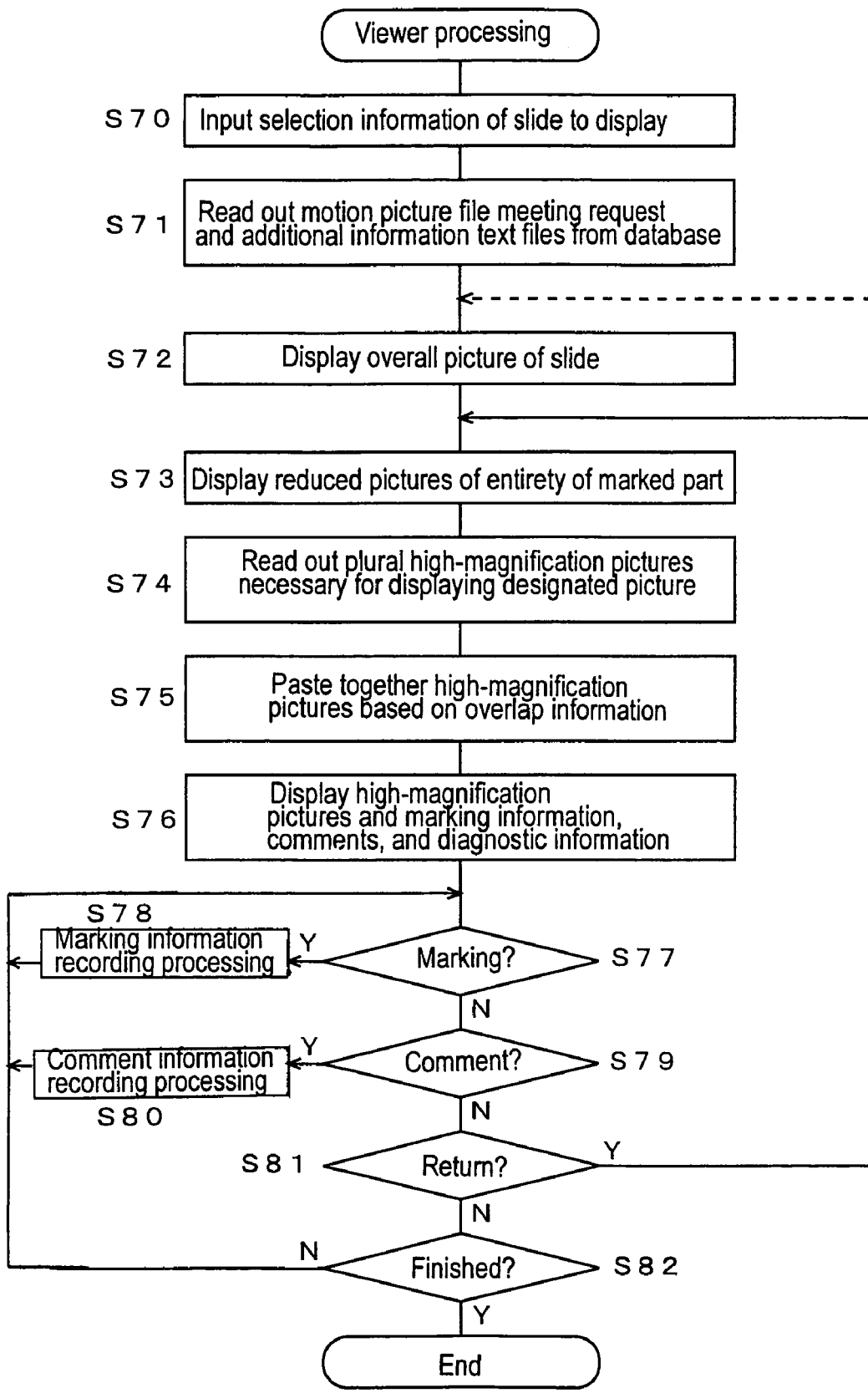
FIG. 14 is a flow chart showing the steps associated with viewer processing according to the present invention.

FIG. 14 is a flow chart showing the steps associated with view processing according to the present invention. The processing is executed, for example, in the personal computer 82 or the terminal (PC) 52. In S70, the slide selection information to be displayed as input-operated by the user is input. The user also may search the database 51 based on keywords such as patient name, and the like. In S71, the motion picture file meeting the request, and additional information text files, such as text files saving diagnostic information, text files saving marking information and comment information and the like, are read out from the database. In S72, the loupe picture (i.e., the overall picture of the slide) is displayed.

FIG. 15 is an explanatory drawing showing an example of a file structure and a picture that is displayed. The loupe picture 63 includes the entirety of the preparate sample. In the loupe picture 63, the marked areas 64 and 65 are set either automatically or manually, and have high-magnification pictures photographs made of the areas. The user clicks, for example, inside the marked area 64 to select it.

In S73, thumbnail pictures 70 (i.e., reduced pictures of the entirety of the marked area part) are displayed. The thumbnail pictures 70 in the middle of FIG. 15, for example, are reductions of 4×4=16 high-magnification pictures pasted together, and the dotted lines 71 and 72 are the boundaries of the high-magnification pictures which are not displayed. The user here clicks, for example, the part of the thumbnail picture 70 one wants to see (e.g., center of area 73).

In S74, plural high-magnification pictures necessary for displaying the designated position at an arbitrary magnification designated by the user are determined, and those pictures are read out. For example, in order to display area 73, four high-magnification pictures are necessary. In S75, the read-out high-magnification pictures are pasted together based on the embedded overlap information.

In S76, the pasted-together high-magnification pictures 75 as well as marking information, comments, and diagnostic information are displayed by being shaped to meet the picture size. The display area can be moved up and down, and left and right, in a state in which the high-magnification pictures 75 are displayed. Also, movement in the Z axis direction is based on instructions to move upward (front side of the screen) or downward (back side of the screen), and the pictures after movement are displayed having been pasted together.

In S77, it is determined as to whether or not there is a marking request, and if the result of the determination is negative, the process moves to S79, and if the result is positive, the process moves to S78. In S78, marking information recording processing is performed. Marking is a function enabling marking (colors, forms, and the like) on a picture. The content of the marking information consists, for example, of marking numbers, X axis position, Y axis position, Z axis position, marking shape and color, line thickness, and the like. The marking information is not applied to the original picture; rather, it is saved as layer information.

In S79, it is determined as to whether or not there is a comment request, and if the result of the determination is negative, the process moves to S81, and if the result is positive, the process moves to S80. In S80, comment information to memorialize the processing is performed. The user records the comments in a comment box displayed on a separate screen. The comment information also is saved as layer information.

In S81, it is determined as to whether or not to return to the display of the entire picture, and if the result of the determination is negative, the process moves to S82, and if the result is positive, the process moves to S73 or S72. In S82, it is determined as to whether or not to end processing, and if the result of the determination is negative, the process moves to S77, and if the result is positive, the processing ends.

When accessing the system from an external terminal 56 over the Internet, the above-described viewer program may be installed on the terminal 56, and the necessary files may be downloaded from the database 51. But, the system may also be configured such that the same function as the viewer program is executed on a web server 50, and a standard web browser is started on the terminal 56 to access the web server. On the web server, screen data to be displayed is created and is sent to the terminal 56 based on operating information from the browser. If the system is configured in this manner, browsing of pictures from any terminal connected to the Internet is possible, without needing to install a custom program.

Figure 16:
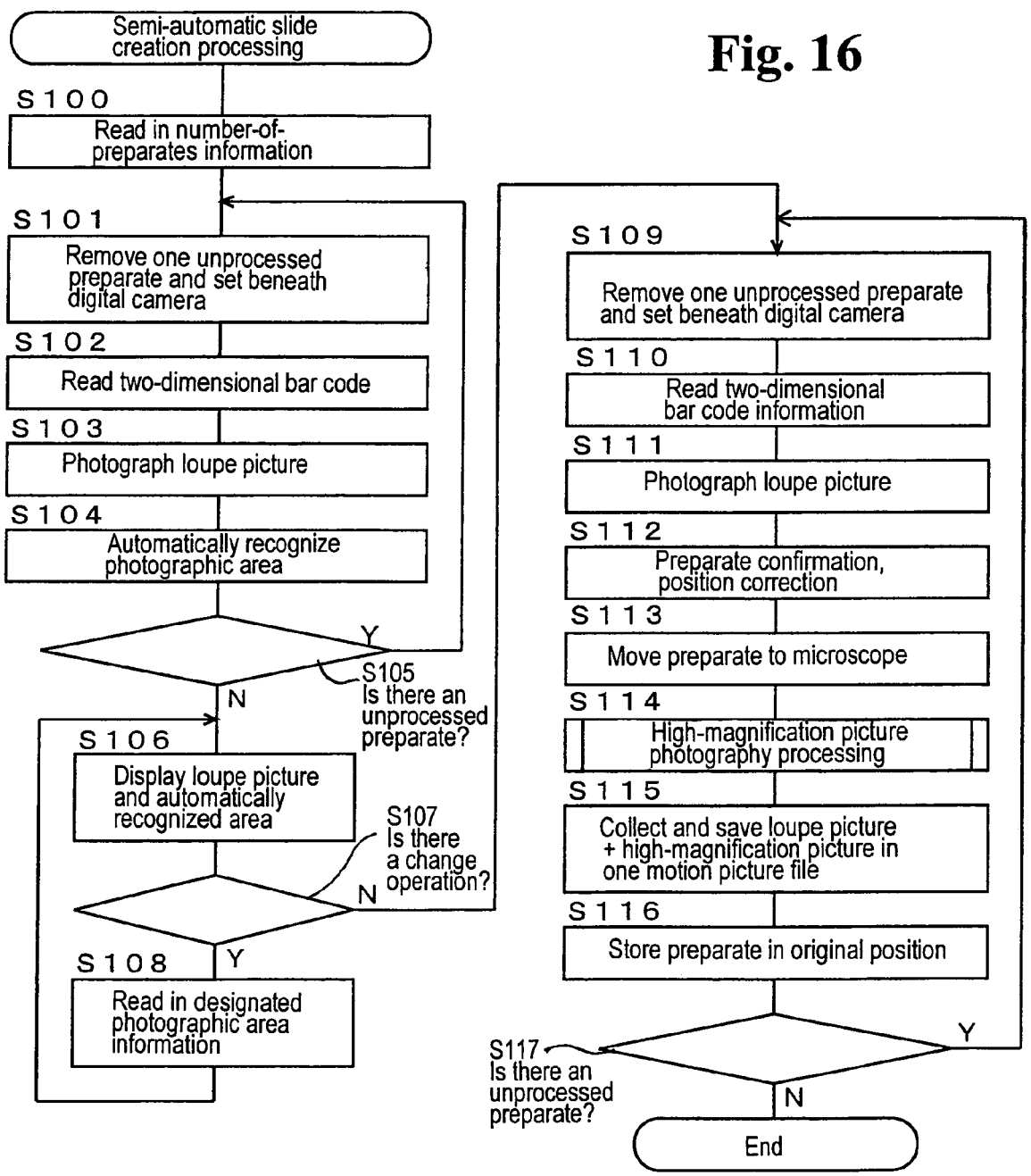
FIG. 16 is a flow chart showing the steps associated with semi-automatic slide creation processing according to a second embodiment of the present invention.

FIG. 16 is a flow chart showing the steps associated with semi-automatic slide creation processing according to a second embodiment of the present invention. In the above-described first embodiment of the invention, an embodiment was disclosed in which marked areas for photographing high-magnification pictures are automatically recognized. But, if all areas of the sample are to be photographed at high magnification, much time is involved, and the amount of data also becomes very great. Therefore, by configuring the system such that first only the loupe pictures are list-displayed for all of the preparates, the user can mark only the parts requiring high-magnification pictures for the respective loupe pictures. The photography time can therefore be shortened, and the amount of data reduced.

Therefore, according to the second embodiment of the invention, in S100, the number-of-preparates information input by the user is read in. In S101, the three-dimensional movement mechanism 7 is controlled and one unprocessed preparate 90 is removed and is placed beneath the digital camera 81. In S102, the two-dimensional bar code is read using the digital camera 81.

In S103, a loupe picture is photographed using the digital camera 81, and the preparate is stored in the original storage position. In S104, the photographic area is automatically recognized. In S105, it is determined as to whether or not there is an unprocessed preparate, and if the result of the determination is positive, the process moves to S101, and if the result is negative, the process moves to S106.

In S106, the loupe pictures and automatically recognized areas of all of the preparates are displayed. The user here marks only the parts requiring photography of high-magnification pictures for the loupe pictures where one wants to change the automatically recognized areas. In S107, it is determined as to whether or not there was a change operation, and if the result of the determination is positive, the process moves to S108, and if the result is negative (i.e., change operations completed), the process moves to S109. In S108, the input photographic area information is read in, the photographic area information is updated, and the process moves to S106.

In S109, the three-dimensional movement mechanism 7 is controlled, and one unprocessed preparate 90 is removed and is set beneath the digital camera 81. In S110, the two-dimensional bar code is read using the digital camera 81. In S111, a loupe picture is photographed using the digital camera 81.

In S112, the previously read two-dimensional bar code is checked to confirm the identification of the preparate. In addition, shifting of position between the loupe picture photographed in S103 and the loupe picture photographed in S111 is detected, and the position of movement by the three-dimensional movement mechanism 7 is corrected based on the detection values.

In S113, the preparate is moved beneath the object lens 2A of the microscope 2. In S114, the previously described high-magnification photography processing is performed. At this time, thumbnail pictures made by pasting together the high-magnification pictures are generated. In S115, the loupe picture+thumbnail pictures+high-magnification pictures are collected in one motion picture file, and it is registered and saved in the database 51.

In S116, the three-dimensional movement mechanism 7 is controlled and the preparate is stored in the original position. In S117, it is determined as to whether or not there is an unprocessed preparate, and if the result of the determination is negative, the processing ends, and if the result is positive, the process moves to S109.

First and second embodiments of the present invention have been described herein, but modified embodiments of the invention as described below are also contemplated. For example, in the first and second embodiments of the invention, tilt and rotation of pictures was not considered. But, the system may also be configured such that relative tilt (rotation) of pictures between a loupe picture and a high-magnification picture, or between adjacent high-magnification pictures, is detected and corrected. Also, lens error correction and color correction, and the like, may also be performed.

In the first embodiment of the invention disclosed herein, about 10 photographs are taken in the up-down-direction centered on the Z axis focal position, and a total of about 20 pictures are stored. But, in another possible embodiment of the invention, by placing a button for moving in the Z axis direction on the viewer, it becomes possible to display pictures moving continuously in the up-down direction. In addition, by composing plural pictures in the Z axis direction, a clear stereo picture can be obtained as two-dimensional data in a sample having more thickness, and it becomes possible also to browse with a viewer.

With regard to the viewer, it is also possible to apply picture corrections such as brightness correction, contrast correction, shading correction, and the like, if the loupe pictures, thumbnail pictures, and high-magnification pictures displayed do not match the picture quality sought by the operator. Also, it is possible to extract a picture from a scope that is being browsed, and remove it to another recording medium as a separate file.

With regard to the loupe pictures, by automatically recognizing the photographic area on a pathological sample, and also computing the optimal photographic position on a blood smear sample from two-valued histogram values and a histogram after RGB decomposition, the optimally distributed position of white blood cells and red blood cells can be recognized.

The slide picture data creation system of the present invention can be used widely in all fields using microscopes, such as, for example, medicine (pathology, hematology, parasitology, etc.), agriculture, pharmacology, physical science, education, and similar disciplines.

The disclosures of Japanese Patent Application No. 2004-11137 filed on Apr. 5, 2004, and Japanese Patent Application No. 2005-113354 filed on Apr. 11, 2005, are incorporated herein.

While the invention has been explained with reference to the specific embodiments of the invention, the explanation is illustrative and the invention is limited only by the appended claims.

What is claimed is:

1. A slide photograph data creation system, comprising:
digital photography means provided in a microscope, for photographing high-magnification photographs of samples;
sample transport means for holding and transporting said samples three-dimensionally;
photography control means for controlling said digital photography means to photograph a plurality of said high-magnification photographs with a predetermined interval, and for controlling said sample transport means to successively move said samples perpendicularly to an optical axis of said microscope to provide a margin where one of said photographs partly overlaps with another of said photographs, said sample transport means also moving the sample minutely along the optical axis of said microscope in each of locations where the sample is moved perpendicular to the optical axis, to thereby obtain the three-dimensional high-magnification photographs;
pasting information generation means for recognizing said margin by photograph processing from said plurality of high-magnification photographs, and for generating pasting information of said plurality of high-magnification photographs;
external digital camera means for photographing an entire image of said samples, different from the digital photography means, and
photograph file generation means for storing in one file said entire image of said samples, said plurality of high-magnification photographs and said pasting-together information.

2. The slide photograph data creation system according to claim 1, further comprising focal position detection means for detecting a position where focus of said microscope is matched in a direction parallel to the optical axis of said microscope.

3. The slide photograph data creation system according to claim 1, further comprising thumbnail photograph generation means for generating reduced-size photographs of an entire photograph by pasting together said high-magnification photographs.

4. The slide photograph data creation system according to claim 1, wherein said photographs made by said external digital camera means, and said plurality of high-magnification photographs, and said pasting information are stored by being combined in a single motion picture file.

5. The slide photograph data creation system according to claim 1, further comprising photographic area automatic recognition means for automatically determining, from the image made by said external digital camera means, an area to photograph said high-magnification photograph.

6. The slide photograph data creation system according to claim 5, further comprising photographic area semi-automatic recognition means for list-displaying said external digital camera photograph for plural preparates together with a photographic area recognized by said photographic area automatic recognition means, to correct said photographic area.

7. The slide photograph data creation system according to claim 1, further comprising photograph publishing means for registering files of said photographs in a database, and for enabling searching and referencing of said photographs over a network.

8. The slide photograph data creation system according to claim 1, wherein said sample transport means comprises:
a first guide member in a fixed position on a stand;
a first movable body, supported to be guided on said first guide member, to move horizontally in a front-back direction of said stand;
a second guide member on said first movable body;
a second movable body, supported to be guided on said second guide member, to move horizontally in a left-right direction of said stand;
a preparate holding hand provided on said second movable body to ascend and descend, said preparate holding hand comprising a pair of finger parts for respectively supporting two ends of a preparate horizontally from beneath, and a suction hole, provided on an upper side of at least one of said finger parts, communicating with a negative pressure source for suction-holding said preparate;
a third guide member in a fixed position on said stand; and
a third movable body, supported to be guided on said third guide member to ascend and descend on said stand.

9. The slide photograph data creation system according to claim 8, further comprising a preparate storage magazine, supported on said third movable body and comprising a pair of side wall plates having plural preparate holding slots arranged in parallel vertically for holding each end of said preparate to receive plural preparates arranged vertically in a shelf-like manner at a vertical spacing such that said finger parts can be inserted and removed.

10. The slide photograph data creation system according to claim 9, wherein said preparate storage magazine is attached to and detached from said third movable body.

11. The slide photograph data creation system according to claim 9, wherein said storage magazine comprises:
an attachment/detachment lever to be manually switched for displacement between a locked position for fixing said magazine to said third movable body, and an unlocked position for releasing said magazine from said third movable body; and
a movable stopper operationally linked to said displacement of the attachment/detachment lever for preventing release of said preparates from the magazine when said attachment/detachment lever is in the unlocked position, and for enabling insertion and removal of said preparates when said attachment/detachment lever is in the locked position.

* * * * *